US010464870B2

(12) United States Patent
Liu et al.

(10) Patent No.: US 10,464,870 B2
(45) Date of Patent: Nov. 5, 2019

(54) METHODS FOR PREPARING DIOL

(71) Applicants: Changchun Meihe Science and Technology Development Co., LTD, Jilin (CN); The Coca-Cola Company, Atlanta, GA (US)

(72) Inventors: Jing Liu, Changchun (CN); Hongbin Qi, Changchun (CN); Haiyu Ren, Atlanta, GA (US); Indra Prakash, Alpharetta, GA (US); Yu Shi, Marietta, GA (US)

(73) Assignees: The Coca-Cola Company, Atlanta, GA (US); Changchum Meihe Science and Technology Development Co., LTD, Jilin (CN)

( * ) Notice: Subject to any disclaimer, the term of this patent is extended or adjusted under 35 U.S.C. 154(b) by 0 days.

(21) Appl. No.: 15/514,980

(22) PCT Filed: Sep. 23, 2015

(86) PCT No.: PCT/CN2015/090321
§ 371 (c)(1),
(2) Date: Mar. 28, 2017

(87) PCT Pub. No.: WO2016/045583
PCT Pub. Date: Mar. 31, 2016

(65) Prior Publication Data
US 2017/0210687 A1 Jul. 27, 2017

(30) Foreign Application Priority Data
Sep. 28, 2014 (CN) .......................... 2014 1 0512704

(51) Int. Cl.
C07C 29/00 (2006.01)
B01J 25/02 (2006.01)
(Continued)

(52) U.S. Cl.
CPC ............. C07C 29/00 (2013.01); B01J 23/835 (2013.01); B01J 23/888 (2013.01);
(Continued)

(58) Field of Classification Search
None
See application file for complete search history.

(56) References Cited

U.S. PATENT DOCUMENTS

2005/0244312 A1* 11/2005 Suppes ................. C07C 29/145
422/198
2012/0172588 A1 7/2012 Qiao et al.
(Continued)

FOREIGN PATENT DOCUMENTS

CN 1683293 10/2005
CN 101199930 6/2008
(Continued)

OTHER PUBLICATIONS

CN102731258 machine translation (translation from 2018 from Google patents).*
(Continued)

Primary Examiner — Clinton A Brooks
(74) Attorney, Agent, or Firm — King & Spalding

(57) ABSTRACT

Provided is a method for preparing a diol. In the method, a saccharide and hydrogen as raw materials are contacted with a catalyst in water to prepare the diol. The employed catalyst is a composite catalyst comprised of a main catalyst and a cocatalyst, wherein the main catalyst is a water-insoluble acid-resistant alloy; and the cocatalyst is a soluble tungstate and/or soluble tungsten compound. The method uses an acid-resistant, inexpensive and stable alloy needless of a support as a main catalyst, and can guarantee a high yield of the diol in the case where the production cost is relatively low.

17 Claims, 1 Drawing Sheet

(51) Int. Cl.
B01J 23/835 (2006.01)
B01J 23/888 (2006.01)
B01J 27/19 (2006.01)
C07C 31/20 (2006.01)
B01J 37/04 (2006.01)
B01J 35/00 (2006.01)
B01J 27/188 (2006.01)
C07C 29/132 (2006.01)
C07C 29/60 (2006.01)
B01J 23/30 (2006.01)
B01J 37/00 (2006.01)

(52) U.S. Cl.
CPC ........... *B01J 23/8885* (2013.01); *B01J 25/02* (2013.01); *B01J 27/188* (2013.01); *B01J 27/19* (2013.01); *B01J 35/0006* (2013.01); *B01J 37/04* (2013.01); *C07C 29/132* (2013.01); *C07C 29/60* (2013.01); *C07C 31/202* (2013.01); *B01J 23/30* (2013.01); *B01J 37/0081* (2013.01); *B01J 2523/00* (2013.01); *Y02P 20/52* (2015.11); *Y02P 20/582* (2015.11)

(56) References Cited

U.S. PATENT DOCUMENTS

2015/0057469 A1 2/2015 Zhang et al.
2017/0203283 A1 7/2017 Liu et al.

FOREIGN PATENT DOCUMENTS

| CN | 101735014 | 6/2010 |
|---|---|---|
| CN | 102190562 | 9/2011 |
| CN | 102731258 | 10/2012 |
| CN | 103848720 | 6/2014 |
| JP | 3293846 | 6/2002 |
| KR | 20020024848 | 4/2002 |
| WO | WO 2013170767 | 11/2013 |
| WO | WO 2015154258 | 10/2015 |

OTHER PUBLICATIONS

International Search Report for PCT/CN2015/090321, dated Dec. 23, 2015.
International Search Report for PCT/CN2015/090323, dated Jan. 4, 2016.
Extended European Search Report for EP1584408.3, dated Apr. 23, 2018.
Extended European Search Report for EP15844730, dated May 2, 2018.
Chapparo, et al. "Data results and operational experience with a solar hydrogen system," J. Power Sources, vol. 144, No. 1, 2005, pp. 165-169.
Corma, et al., "Chemical Routes for the Transformation of Biomass into Chemicals" Chemical Reviews, vol. 107, No. 6, 2007, pp. 2411-2502.
Zhijun, T., et al. "Catalytic Conversion of Cellulose to Ethylene Glycol over a Low-Cost Binary Catalyst of Raney Ni and Tungstic Acid", CHEMSUSCHEM, vol. 6, No. 4, 2013, pp. 652-658.
Mingyuan Zheng, Jifeng Pang, Aiqin Wang, Tao Zhang, Chinese Journal of Catalysis 35 (2014) 602-613.
Yan, L., et al. "Studies on Mechanism of Sucrose Decomposition in Impure Sugar Solutions", China and Beet Sugar, 1996, pp. 11-16.

* cited by examiner

METHODS FOR PREPARING DIOL

CROSS REFERENCE TO RELATED APPLICATIONS

This application is a national phase application under 35 U.S.C. § 371 of International Application No. PCT/CN2015/090321, filed on Sep. 23, 2015, which claims priority to Chinese Patent Application No. 201410512704.7, filed Sep. 28, 2014. The complete disclosure of each of the above-identified applications is fully incorporated herein by reference.

TECHNICAL FIELD

The present invention relates to a method for preparing a diol.

BACKGROUND ART

Ethylene glycol, as an important monomer for bottle-grade polyester and fiber-grade polyester, has a very large application market. Propylene glycol may be widely used in the food, pharmaceutical and cosmetics industries. For a long time now, diols such as ethylene glycol and propylene glycol have been mainly produced using petroleum-based olefins as starting materials, by methods such as the two step method of oxidation and hydration. However, as petroleum resources are gradually depleted, the utilization of renewable starting materials to prepare diols has huge commercial prospects.

A process for preparing ethylene glycol by one-step catalytic hydrocracking, using soluble sugar as a starting material, has been disclosed in the prior art. The process is simple and the starting material is abundant, so the process has prospects for large-scale commercial production. However, the process has various deficiencies. For example, starting material sugars are of low concentration (e.g. WO 2013015955 A, CN 102020531 A), a precious metal or a combination of a precious metal and a cheap metal is used as a catalyst (e.g. U.S. Pat. No. 4,496,780 A, CN 102643165 A, CN 103420797 A), the ethylene glycol yield is low (e.g. U.S. Pat. No. 4,496,780 A, CN 102731259 A, CN 103420787 A, CN 101735014 A, CN 101613253 A, CN 103667365 A), etc., so that the ethylene glycol production cost is too high, the catalyst activity is unstable, and continuous production is not possible.

Research has found that in a process for preparing a diol by one-step catalytic hydrocracking of soluble sugar, starting material sugar very readily undergoes side reactions such as hydrolysis under high-temperature aqueous phase conditions, producing small-molecule substances such as acetic acid, lactic acid, formic acid, furan, aldehydes and alcohols etc., in turn leading to an increase in the acidity of the system (Sevilla M, Fuertes A B. Chemical and structural properties of carbonaceous products obtained by hydrothermal carbonization of saccharides. Chemistry-A European Journal. 2009, 15(16): 4195-4203.). At the same time, polymers formed by further condensation polymerization of the aldehydes and alcohols etc. produced will block catalyst pores, and this will lower the catalyst's catalytic activity, service life and selectivity as well as the long-term operational stability of the reaction system; the result is that the process has poor economic feasibility, and cannot be used for large-scale, continuous production. At the same time, the production of by-products also leads to a drop in the diol yield. It is disclosed in existing patent applications that 40-60% of the starting material sugar will undergo a hydrolysis side reaction (U.S. Pat. No. 5,107,018, CN 101781167 A, CN 101781171 A, CN 101781166 A).

When the concentration of starting material sugar is high, under high-temperature aqueous phase conditions, in the first place it more easily undergoes polymerization and thereby blocks catalyst channels, leading to a shortening of the life of the catalyst, and an increase in the production cost of diols, and for this reason the requirements for catalytic activity of the catalyst are higher in order that the starting material sugar is hydrocracked before it undergoes polymerization. In the second place, acid of higher concentration is produced more easily, and for this reason the requirements for acidity resistance of the catalyst are higher. Therefore, in most existing patent applications, sugar of low concentration is used as a starting material. For example, CN 102190562 A and CN 101735014 A employ a composite catalyst formed of a tungsten compound and an active component, and a monosaccharide of 1% glucose etc. dissolved in water as a starting material, and the ethylene glycol yield is 30-45%. CN 103420796 A employs a composite catalyst of Ru/C and tungstic acid, and a monosaccharide of 1% glucose etc. dissolved in water as a starting material; the catalyst is recycled intermittently, and the ethylene glycol yield is 52-57%. CN 102731258 A employs an Ni—$W_2C$/AC supported catalyst, and 18% glucose as a starting material, and the diol yield is 50-60%, wherein the ethylene glycol yield is 55%. These applications have good ethylene glycol yields, but have the following shortcomings due to the low concentration of starting material sugar used: Firstly, the glucose concentration is 1-18%, so the reaction system contains a large amount of water; the boiling point of ethylene glycol is higher than that of water, being 197.3° C., so when separation by rectification is performed, the system must first consume a large amount of heat in distilling off the water, leading to high separation costs, so production is not economical. Secondly, these applications all use activated carbon as a support, but activated carbon readily undergoes a hydrogenation reaction under high-temperature conditions in the presence of hydrogen, thereby being methanized (US2002/0169344). The existing patent application CN 102643165 A has disclosed the use of 40-60% glucose as a starting material, and the diol yield is 50-60%; however, that application uses Ru/C with an activated carbon support as the catalyst; using a precious metal as a catalyst will make the production cost high, there is a risk of the activated carbon being methanized, and the continuous operational stability of that application is unknown.

In processes for preparing diols by one-step catalytic hydrocracking of soluble sugar, commonly used catalysts include cheap metals (such as nickel) and precious metals. In the case where a nickel-containing catalyst is used as a catalyst, when the acidity of the reaction system increases due to starting material sugar undergoing a hydrolysis side reaction, the nickel will undergo a reaction, releasing hydrogen and producing nickel ions $Ni^{2+}$, so that the nickel-containing catalyst slowly dissolves, losing its hydrogenating activity. It has been reported in the literature that the reaction system pH may be regulated at 7 or higher to maintain the stability of the nickel-containing catalyst (CN 103667365 A). Under high pH conditions, the propylene glycol yield will increase significantly while the ethylene glycol yield will decrease significantly (U.S. Pat. No. 5,107,018, CN 101781167 A, CN 101781171 A, CN 101781166 A); at the same time, acids produced in the hydrolysis side reaction such as formic acid, acetic acid and lactic acid will increase, and the total diol yield will fall (CN 101544537 A).

Li Yan et al. have found that under acidic conditions of pH<5, the starting material sugar is in a more stable state, and essentially does not undergo a hydrolysis side reaction (Li Yan, Shen Canqiu et al., Research on the decomposition mechanism of sucrose in impure sugar solutions, China Beet and Sugar, 1996(2): 11-16); thus, the diol yield of a sugar hydrocracking system can be increased if the latter operates under acidic conditions. When a precious metal such as Ru or Pt is used as a catalyst, it can exist stably under low pH conditions, but will significantly increase the diol production cost. To reduce the amount of precious metal used and increase its catalytic activity, people select supports with a high specific surface area to fix and disperse it. An example of commonly used supports is inorganic oxides such as alumina, silica and magnesia, which are unstable under acidic conditions, and readily undergo a neutralization reaction and dissolve in the reaction system, leading to a fall in the diol yield (CN 103159587 A); another example is activated carbon (CN 103420796 A, CN 102643165 A, CN 102731258 A, CN 101613253 A), which readily undergoes a hydrogenation reaction and is methanized under high-temperature conditions in the presence of hydrogen.

In summary, a new diol preparation method is needed. A diol is produced at low cost through the use of an acid-resistant, cheap and stable catalyst.

Content of the Present Invention

The object of the present invention is to provide a method for preparing a diol. The present invention uses an acid-resistant, cheap and stable alloy, which does not need a support, as a main catalyst to prepare a diol.

The present invention employs the following technical solution:

A method for preparing a diol, which method uses a sugar and hydrogen as starting materials, which are brought into contact with a catalyst in water to prepare a diol; the catalyst used is a composite catalyst, consisting of a main catalyst and a cocatalyst, wherein the main catalyst is a water-insoluble acid-resistant alloy;

the cocatalyst is a soluble tungstic acid salt and/or an insoluble tungsten compound.

Preferably, the diol is ethylene glycol.

The present invention uses an acid-resistant, cheap and stable alloy, which does not need a support and is insoluble in water, as a main catalyst, which is used in cooperation with a cocatalyst of a soluble tungstic acid salt and/or an insoluble tungsten compound, to catalyse sugar as a composite catalyst to obtain a diol; the yield of diol, in particular ethylene glycol, can be ensured at a low production cost. The water-insoluble, acid-resistant alloy of the present invention is stable under acidic conditions, and there is no need to add an alkali to the reaction system to neutralize acid formed by hydrolysis of sugar. When the method of the present invention is used in continuous industrial production, the use of such an acid-resistant alloy main catalyst is especially important for the long-term, stable operation of the system and for control of production costs.

Preferably, when ethylene glycol is prepared by the method described above, the reaction system pH is 1-7; more preferably, the reaction system pH is 3-6. By keeping the system pH<7, not only can a hydrolysis side reaction of starting material sugar during the reaction be avoided, thereby reducing the amount of starting material sugar consumed in ethylene glycol production, but also the service life of the catalyst is ensured, so the cost of using the catalyst can be reduced, the stability of long-term continuous operation of the reaction system can be ensured; at the same time, the ethylene glycol yield is high, and the output of organic acids and polymers is low. If acids produced in the course of the reaction are not enough to maintain a low pH, inorganic acids or organic acids such as lactic acid, formic acid and acetic acid may be added to the system to regulate the pH of the reaction system. Generally, organic acid or inorganic acid is added together with starting material sugar.

Preferably, the sugar is selected from one or more of five-carbon monosaccharides, disaccharides and oligosaccharides, six-carbon monosaccharides, disaccharides and oligosaccharides, soluble five-carbon polysaccharides, and soluble six-carbon polysaccharides. Original sources of the starting material sugar include but are not limited to sugar-based substances such as beet and sugarcane, starch-based substances such as maize, wheat, barley and cassava, ligno-cellulose-based substances such as maize straw, corn cobs, wheat straw, sugarcane dregs and timber, cellulosic industrial residue such as corn cob dregs, or polysaccharide substances including algae, etc. In this text, soluble five-carbon polysaccharides and soluble six-carbon polysaccharides are five-carbon polysaccharides and six-carbon polysaccharides which can dissolve under the reaction conditions of the present invention, not just five-carbon polysaccharides and six-carbon polysaccharides which can dissolve at room temperature.

Preferably, the sugar reacts with hydrogen in the form of an aqueous sugar solution (abbreviated as sugar solution), and the aqueous sugar solution has a concentration of 5-60 wt %, more preferably 20-50 wt %. In a continuous operation, the sugar solution may be fed continuously by means of a delivery pump. In the present invention, a suitable catalyst is selected so that the restriction imposed on starting material sugar concentration by the reaction system is smaller; sugar solution of high concentration may be used as a starting material, and this will significantly reduce the production cost of diol, in particular ethylene glycol, thereby realizing large-scale and economical diol production.

Furthermore, the acid-resistant alloy comprises nickel, one or more rare earth elements, tin and aluminum; the parts by weight of the components are preferably 10-90 parts, 1-5 parts, 1-60 parts and 5-9 parts respectively.

In this text, rare earth elements is a collective term for 17 chemical elements, with atomic numbers 21, 39 and 57-71, in group IIIB of the periodic table, including lanthanum (La), cerium (Ce) and samarium (Sm) etc.

More preferably, the acid-resistant alloy comprises nickel, one or more rare earth elements, tin, aluminum and tungsten; the parts by weight of the components are preferably 10-90 parts, 1-5 parts, 1-60 parts, 5-9 parts and 1-90 parts respectively.

Further preferably, the acid-resistant alloy comprises nickel, one or more rare earth elements, tin, aluminum, tungsten and molybdenum; the parts by weight of the components are preferably 10-90 parts, 1-5 parts, 1-60 parts, 5-9 parts, 1-90 parts and 0.5-20 parts respectively.

Most preferably, the acid-resistant alloy comprises nickel, one or more rare earth elements, tin, aluminum, tungsten, molybdenum, and boron or phosphorus; the parts by weight of the components are preferably 10-90 parts, 1-5 parts, 1-60 parts, 5-9 parts, 1-parts, 0.5-20 parts and 0.01-5 parts respectively.

Preferably, the soluble tungstic acid salt is one or more of ammonium tungstate, sodium tungstate and sodium phosphotungstate; the insoluble tungsten compound is tungsten trioxide and/or tungstic acid.

The main catalyst is mixed with water and then added to a reactor.

Preferably, the amount of the main catalyst used is 0.01-10 times the amount of sugar fed per hour.

Preferably, the reaction is in continuous mode.

Preferably, the amount of main catalyst added is: 0.01-5 kg of main catalyst added per 1000 kg of sugar fed. The addition of catalyst may be realized by discharging a portion of old catalyst through a catalyst output valve (generally at the bottom of the reactor), then adding the same amount of new catalyst through a catalyst feed valve (generally at the bottom of the reactor.

The soluble cocatalyst may be first added to sugar solution, then these may be added to the reactor together. Preferably, the amount of the soluble cocatalyst used is 0.01-5 wt % of the aqueous sugar solution, more preferably 0.01-2 wt %, and most preferably 0.01-1 wt %.

The insoluble cocatalyst may be added to the reactor together with the main catalyst. Preferably, the amount of the insoluble cocatalyst used is 0.5-50 wt % of the main catalyst, more preferably 5-20 wt %.

Preferably, the reaction system has a reaction pressure of 5-12 MPa, a reaction temperature of 150-260° C., and a reaction time 10 min.

More preferably, the reaction system has a reaction pressure of 6-10 MPa, a reaction temperature of 180-250° C., and a reaction time of 0.5-3 h. The reaction time is most preferably 0.5-2 hours.

Preferably, the reaction takes place in a slurry bed reactor. To ensure that the reaction proceeds smoothly, the total volume of reaction liquid formed does not exceed 80% of the reactor volume.

Preferably, a filter is provided in the slurry bed reactor, for causing an insoluble portion of the catalyst to be retained in the reactor, and not carried away by gas and reaction liquid flowing out through the filter.

Before the reaction begins, main catalyst is added to the slurry bed reactor, and hydrogen and sugar solution are added to the reactor at the same time using respective pumps, and a reaction takes place; the addition of sugar and main catalyst is in a continuous flow state, and reaction liquid flows out of the reactor continuously. Regarding the cocatalyst, when it is a soluble tungsten compound, it is added to the reactor together with sugar solution; when it is an insoluble tungsten compound, it is added to the reactor at the same time as the main catalyst. A filter is installed in the reactor. The filter can intercept catalyst, but gas and reaction liquid will flow out continuously through the filter and enter a condenser to undergo gas/liquid separation. Crude hydrogen undergoes purification to remove CO, $CO_2$ and $CH_4$ etc., and becomes purified hydrogen again, returning to the reactor. Effluent flowing out of the condenser enters a separation system, and is separated to obtain water, ethylene glycol, propylene glycol, butylene glycol, glycerol, sorbitol and cocatalyst, etc. Products such as ethylene glycol, propylene glycol and butylene glycol may be obtained by purification using existing technology (e.g. rectification). Water, sorbitol, glycerol and cocatalyst that is already dissolved in the reaction system are returned to the reactor to react in a cycle.

The beneficial effects of the present invention are as follows:

1. The catalyst of the present invention is cheap, stable, and does not need a support.

2. The present invention can use a sugar solution of high concentration as a starting material, so the production cost of diols, in particular ethylene glycol, is low.

3. The method of the present invention gives a high ethylene glycol yield.

DESCRIPTION OF THE ACCOMPANYING DRAWINGS

PARTICULAR EMBODIMENTS

The present invention is explained further below in conjunction with the accompanying drawings and embodiments.

Figure 1:
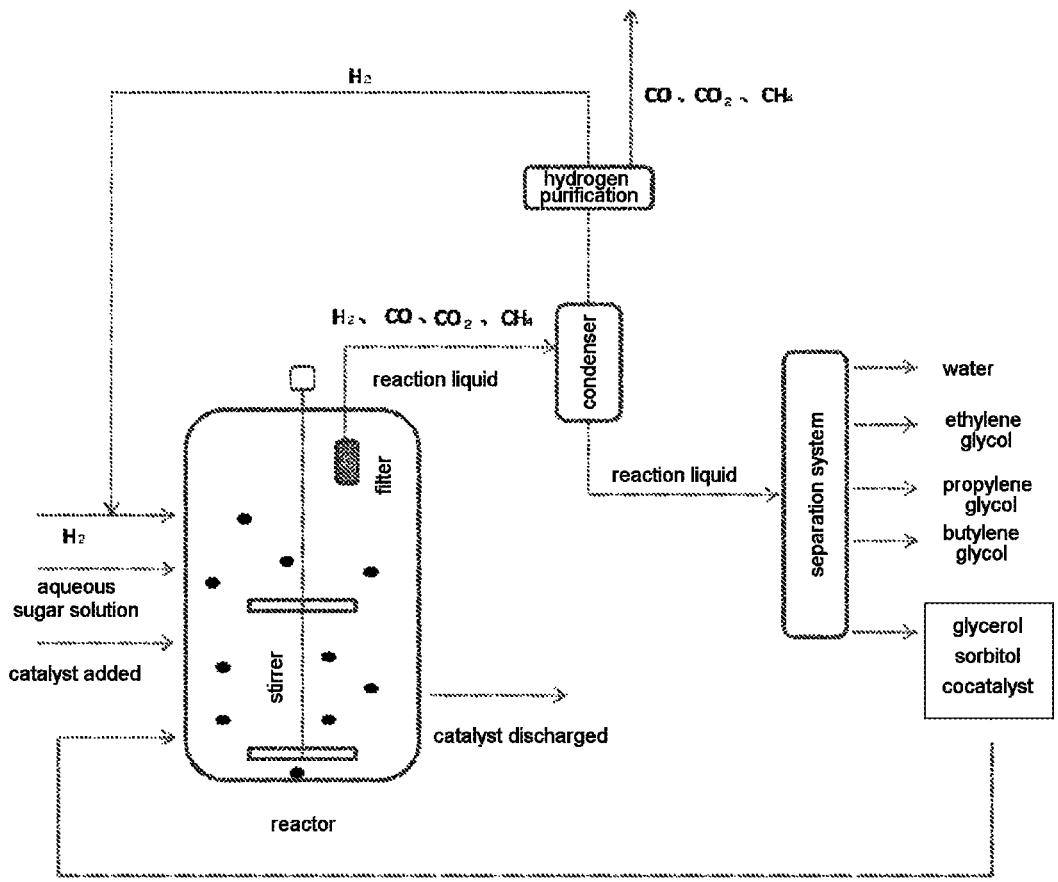
FIG. 1 is a schematic flow chart of the method of the present invention.

FIG. 1 is a schematic flow chart of the method of the present invention.

Embodiment 1

Preparation of Acid-Resistant Alloy Main Catalyst:

With regard to the acid-resistant alloy main catalyst of the present invention, an active metal powder with a high specific surface area can be prepared directly by chemical reduction or electrolytic deposition; alternatively, a metal alloy is formed by smelting, then metal powder is formed by mechanical pulverizing or atomizing, etc., and finally, an active metal powder is formed by a conventional Raney nickel catalyst activation method. For example, in parts by weight, 10-90 parts, 1-5 parts, 1-60 parts, 5-9 parts, 1-90 parts, 0.5-20 parts and 0.01-5 parts of nickel, rare earth element, tin, aluminum, tungsten, molybdenum, and boron or phosphorus respectively are added to a smelting furnace; the temperature is raised to 1500-2000° C., then the temperature is lowered, and after thorough mechanical stirring to achieve uniformity, the furnace is emptied, to obtain he metal alloy. A hammer grinder is used to pulverize the metal alloy into metal powder, which is then immersed for 1-2 hours in a 20 wt %-25 wt % aqueous sodium hydroxide solution at 70-95° C., to form an active metal powder with a high specific surface area.

An acid-resistant alloy main catalyst Ni80La1Sn30Al5 (indicating that the composition of the acid-resistant alloy is 80 parts Ni+1 part La+30 parts Sn+5 parts Al, likewise below), an acid-resistant alloy main catalyst Ni10Sm5Sn3Al9W70Mo5, an acid-resistant alloy main catalyst Ni70Ce1Sn50Al7W5Mo1B5, an acid-resistant alloy main catalyst Ni90Ce3Sn60Al9W20Mo5B1, an acid-resistant alloy main catalyst Ni10Sm5Sn10Al9W90, an acid-resistant alloy main catalyst Ni90Ce3Sn60Al9W20Mo20P0.01, and an acid-resistant alloy main catalyst Ni80La1Ce0.5Sn30Al5 are prepared separately.

Embodiment 2

6 L of water and 1000 g of acid-resistant alloy main catalyst Ni80La1Sn30Al5 are added to a 10 L reaction kettle while stirring. The reaction kettle is sealed, hydrogen is passed in for 5 hours at 1000 L/h at atmospheric pressure to replace air in the reaction kettle, then the hydrogen pressure is raised to 10 MPa, and hydrogen is passed in for a further 5 hours, the reaction kettle temperature is raised to 250° C., and continuous feeding begins. The feed composition is: 50 wt % glucose, 2 wt % sodium tungstate, 48 wt % water, and the density of the sugar solution is about 1.23 g/cm$^3$; the feed rate is 3 L/h. The residence time of sugar in the reaction kettle is 2 hours. Acetic acid is added to the reaction kettle such that the reaction system pH is 3.5. Reaction liquid and hydrogen after the reaction flow out of the reaction kettle through a filter into a condensing tank; the output speed of reaction liquid is L/h, and reaction liquid is discharged from the bottom of the condensing tank after cooling, to give effluent. The effluent enters a rectification separation system, and water, ethylene glycol, propylene glycol, glycerol and sorbitol and sodium tungstate are respectively obtained, wherein heavy components that are not distilled out, including glycerol and sorbitol and sodium tungstate, are returned to the reaction system to react in a cycle. A sample is taken at the bottom of the condensing tank, and the composition thereof is detected by high performance liquid chromatography.

A conventional technique may be used for the high performance liquid chromatography detection. The present invention provides the following experimental parameters for reference:

Instrument: Waters 515 HPLC Pump;
Detector: Water 2414 Refractive Index Detector;
Chromatography column: 300 mm×7.8 mm, Aminex HPX-87H ion exchange column;
Mobile phase: 5 mmol/L sulphuric acid solution;
Mobile phase flow rate: 0.6 ml/min;
Column temperature: 60° C.;
Detector temperature: 40° C.

Results: the glucose conversion rate is 100%; the diol yield is 77%, wherein the ethylene glycol yield is 71%, the propylene glycol yield is 7%, and the butylene glycol yield is 3%; the methanol and ethanol yield is 5%, and other yields are 14%.

Figure 2:
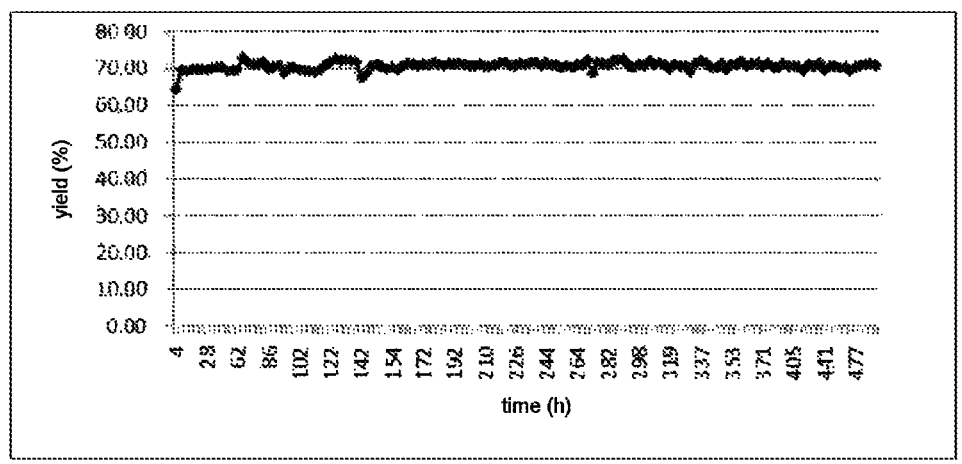
FIG. 2 is a graph of the variation of ethylene glycol yield with time in embodiment 2.

FIG. 2 is a graph of the variation of ethylene glycol yield with reaction system operation time. It can be seen from the figure that the ethylene glycol yield is substantially maintained at about 70%. This indicates that the composite catalyst of the present invention can ensure that the ethylene glycol yield is still stable after 500 hours of continuous operation of the reaction system.

When the reaction system pH is changed to 9, the results are: the glucose conversion rate is 100%; the diol yield is 68%, wherein the ethylene glycol yield is 38%, the propylene glycol yield is 27%, and the butylene glycol yield is 3%; the methanol and ethanol yield is 5%, and other yields are 27%.

Embodiment 3

The acid-resistant alloy main catalyst is Ni10Sm5Sn3Al9W70Mo5, and the amount added is 5000 g.

The feed composition is: 15 wt % glucose, 0.01 wt % ammonium tungstate, 84.9 wt % water, and the density of the sugar solution is about 1.06 g/cm$^3$.

Reaction system pH=6.

Other operating conditions are the same as in embodiment 2.

Results: the glucose conversion rate is 100%; the diol yield is 66%, wherein the ethylene glycol yield is 61%, the propylene glycol yield is 3%, and the butylene glycol yield is 2%; the methanol and ethanol yield is 9%, and other yields are 25%.

Embodiment 4

The acid-resistant alloy main catalyst is Ni70Ce1Sn50Al7W5Mo1B5, and the amount added is 500 g.

The amount of tungsten trioxide added is 100 g.

The feed composition is: 40 wt % glucose, 60 wt % water, and the density of the sugar solution is about 1.18 g/cm$^3$.

Reaction system pH=4.2.

Other operating conditions are the same as in embodiment 2.

Results: the glucose conversion rate is 100%; the diol yield is 70%, wherein the ethylene glycol yield is 67%, the propylene glycol yield is 2%, and the butylene glycol yield is 1%; the methanol and ethanol yield is 9%, and other yields are 21%.

Embodiment 5

The acid-resistant alloy main catalyst is Ni90Ce3Sn60Al9W20Mo5B1, and the amount added is 1000 g.

The feed composition is: 15 wt % xylose, 40 wt % glucose, wt % maltose, 1 wt % maltotriose, 1 wt % sodium phosphotungstate, 42 wt % water, and the density of the sugar solution is about 1.22 g/cm$^3$.

Reaction system pH=4.8.

Other operating conditions are the same as in embodiment 2.

Results: the conversion rate of xylose, glucose, maltose and maltotriose is 100%; the diol yield is 75%, wherein the ethylene glycol yield is 60%, the propylene glycol yield is 11%, and the butylene glycol yield is 4%; the methanol and ethanol yield is 7%, and other yields are 18%. After 500 hours of catalyst operation, the ethylene glycol yield is still stable.

Embodiment 6

The acid-resistant alloy main catalyst is Ni90Ce3Sn60Al9W20Mo5B1, and the amount added is 5000 g.

The feed composition is: 50 wt % xylose, 0.1 wt % sodium tungstate, 49.9 wt % water, and the density of the sugar solution is about 1.21 g/cm$^3$.

Reaction system pH=4.8.

Other operating conditions are the same as in embodiment 2.

Results: the conversion rate of xylose is 100%; the diol yield is 67%, wherein the ethylene glycol yield is 49%, the propylene glycol yield is 16%, and the butylene glycol yield is 2%; the methanol and ethanol yield is 12%, and other yields are 21%. After 500 hours of catalyst operation, the ethylene glycol yield is still stable.

Embodiment 7

The acid-resistant alloy main catalyst is Ni10Sm5Sn10Al9W90, and the amount added is 180 g.

The feed composition is: 60 wt % glucose, 2 wt % sodium tungstate, 38 wt % water, and the density of the sugar solution is about 1.29 g/cm$^3$.

The reaction pressure is 12 MPa, and the reaction temperature is 260° C.

Other operating conditions are the same as in embodiment 2.

Results: the conversion rate of glucose is 100%; the diol yield is 75%, wherein the ethylene glycol yield is 65%, the propylene glycol yield is 7%, and the butylene glycol yield is 3%; the methanol and ethanol yield is 11%, and other yields are 14%.

Embodiment 8

The acid-resistant alloy main catalyst is Ni90Ce3Sn60Al9W20Mo20P0.01, and the amount added is 5 g.

The feed composition is: 5 wt % glucose, 0.05 wt % sodium tungstate, 94.95 wt % water, and the density of the sugar solution is about 1.02 g/cm$^3$.

Reaction system pH=1.

The reaction pressure is 6 MPa, and the reaction temperature is 180° C.

Other operating conditions are the same as in embodiment 2.

Results: the conversion rate of glucose is 100%; the diol yield is 65%, wherein the ethylene glycol yield is 53%, the propylene glycol yield is 9%, and the butylene glycol yield is 3%; the methanol and ethanol yield is 4%, and other yields are 31%.

Embodiment 9

The acid-resistant alloy main catalyst is Ni80La1Ce0.5Sn30Al5; other operating conditions are the same as in embodiment 2.

Results are similar to those of embodiment 2.

Embodiment 10

The acid-resistant alloy main catalyst is Ni70Sm1Sn10Al7W5Mo0.5, and the amount added is 1500 g.

The feed composition is: 40 wt % glucose, 60 wt % water, 0.5 wt % sodium tungstate, and the density of the sugar solution is about 1.18 g/cm$^3$.

Reaction system pH=4.2.

Other operating conditions are the same as in embodiment 2.

Results: the conversion rate of glucose is 100%; the diol yield is 87%, wherein the ethylene glycol yield is 80%, the propylene glycol yield is 5%, and the butylene glycol yield is 2%; the methanol and ethanol yield is 3%, and other yields are 10%.

Clearly, the abovementioned embodiments of the present invention are merely examples given to explain the present invention clearly, and by no means define the embodiments of the present invention. A person skilled in the art could make other changes or modifications in different forms on the basis of the explanation above. It is not possible to list all embodiments here exhaustively. All obvious changes or modifications extended from the technical solution of the present invention shall still fall within the scope of protection of the present invention.

The invention claimed is:

1. A method for preparing a diol comprising contacting a sugar and hydrogen with a catalyst in water in a reactor to prepare a diol; wherein the catalyst is a composite catalyst consisting of a main catalyst and a cocatalyst;

the main catalyst is a water-insoluble acid-resistant alloy comprising nickel, one or more rare earth elements, tin and aluminum; and the cocatalyst is a soluble tungstic acid salt and/or an insoluble tungsten compound.

2. The method of claim 1, wherein the diol is ethylene glycol.

3. The method of claim 2, wherein the pH of the reactor is 1-7.

4. The method of claim 1, wherein the sugar is selected from the group consisting of one or more five-carbon monosaccharides, disaccharides, and oligosaccharides; six-carbon monosaccharides, disaccharides and oligosaccharides; soluble five-carbon polysaccharides and soluble six-carbon polysaccharides.

5. The method of claim 1, wherein the sugar is provided in the form of an aqueous sugar solution, wherein the aqueous sugar solution has a concentration of 5-60 wt %.

6. The method of claim 5, wherein the amount of the soluble cocatalyst used is 0.01-5 wt % of the aqueous sugar solution.

7. The method of claim 6, wherein the amount of the insoluble cocatalyst used is 0.5-50 wt % of the main catalyst.

8. The method for preparing a diol as claimed in claim 1, characterized in that the acid-resistant alloy comprises, in parts by weight, 10-90 parts nickel, 1-5 parts rare earth element, 1-60 parts tin and 5-9 parts aluminum.

9. The method of claim 1, wherein the acid-resistant alloy comprises, in parts by weight, 10-90 parts nickel, 1-5 parts rare earth element, 1-60 parts tin, 5-9 parts aluminum, 1-90 parts tungsten and 0.5-20 parts molybdenum.

10. The method of claim 1, wherein the soluble tungstic acid salt is selected from the group consisting of ammonium tungstate, sodium tungstate, sodium phosphotungstate and combinations thereof.

11. The method of claim 1, wherein the insoluble tungsten compound is selected from tungsten trioxide, tungstic acid and a combination thereof.

12. The method of claim 1, wherein the amount of the main catalyst used is 0.01-10 times the amount of sugar fed per hour.

13. The method of claim 1, wherein the reactor has a reaction pressure of 6-10 MPa, a reaction temperature of 180-250° C., and a reaction time of 0.5-3 h.

14. The method of claim 1, wherein the method is continuous.

15. The method of claim 14, wherein the amount of main catalyst added is: 0.01-5 kg of main catalyst is added per 1000 kg of sugar fed.

16. The method of claim 1, further comprising separating the cocatalyst from the diol and then recycling the cocatylst in a subsequent method.

17. The method of claim 1, wherein the reactor is slurry bed reactor.

* * * * *